US008637251B2

(12) United States Patent
Abe et al.

(10) Patent No.: US 8,637,251 B2
(45) Date of Patent: Jan. 28, 2014

(54) NUCLEIC ACID QUANTIFICATION METHOD AND MICROCHIP FOR NUCLEIC ACID AMPLIFICATION REACTION

(75) Inventors: Tomoteru Abe, Tokyo (JP); Yuji Segawa, Tokyo (JP); Junji Kajihara, Tokyo (JP); Tomohiko Nakamura, Tokyo (JP); Masaki Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 127 days.

(21) Appl. No.: 13/231,179

(22) Filed: Sep. 13, 2011

(65) Prior Publication Data

US 2012/0070841 A1 Mar. 22, 2012

(30) Foreign Application Priority Data

Sep. 16, 2010 (JP) ................................. 2010-207853
Nov. 25, 2010 (JP) ................................. 2010-261934

(51) Int. Cl.
*C12Q 1/68* (2006.01)
*C12P 19/34* (2006.01)

(52) U.S. Cl.
USPC ........................... 435/6.12; 435/6.1; 435/6.11

(58) Field of Classification Search
None
See application file for complete search history.

(56) References Cited

U.S. PATENT DOCUMENTS 7,264,950 B1 * 9/2007 Lee et al. ..................... 435/91.2

FOREIGN PATENT DOCUMENTS

JP 2001-269196 10/2001

OTHER PUBLICATIONS

Vogelstein, et al., "Digital PCR" Proc. Natl. Acad. Sci., vol. 96, pp. 9236-9292, 1999.

* cited by examiner

*Primary Examiner* — Young J Kim
(74) *Attorney, Agent, or Firm* — K&L Gates LLP

(57) ABSTRACT

A nucleic acid quantification method that uses a microchip for nucleic acid amplification reaction, the microchip including an inlet through which a liquid is introduced from outside, a plurality of reaction regions provided as reaction sites of a nucleic acid amplification reaction, and a channel through which the liquid introduced through the inlet is supplied into each of the reaction regions, wherein the likelihood of the nucleic acid amplification reaction varies between the reaction regions, includes: flowing a detection target nucleic acid chain-containing solution through the channel and introducing the solution into each of the reaction regions to perform a nucleic acid amplification reaction; and detecting an amplification product in each of the reaction regions to specify the reaction regions in which the nucleic acid amplification reaction occurred.

1 Claim, 5 Drawing Sheets

NUCLEIC ACID QUANTIFICATION METHOD AND MICROCHIP FOR NUCLEIC ACID AMPLIFICATION REACTION

CROSS REFERENCES TO RELATED APPLICATIONS

The present application claims priority to Japanese Priority Patent Application JP 2010-207853 and JP 2010-261934 filed in the Japan Patent Office on Sep. 16, 2010 and Nov. 25, 2010, respectively, the entire contents of which are hereby incorporated by reference.

BACKGROUND

The present application relates to nucleic acid quantification methods, and microchips for nucleic acid amplification reaction. Specifically, the present application concerns nucleic acid quantification methods for conveniently measuring the approximate amount of the detection target nucleic acid chain contained in a sample.

Nucleic acid amplification methods such as PCR (Polymerase Chain Reaction) have been used in many applications, including the diagnoses of infections and hereditary diseases, gene expression level analyses, and cloning. Real-time nucleic acid amplification methods that measure the amplified amount of the detection target nucleic acid chain in real time based on the increased fluorescence intensity of the fluorescent dye or fluorescent dye-labeled fluorescent probe used for the measurement also have been used for the quantification of the original amount of the detection target nucleic acid chain.

Digital PCR, Proc. Natl. Acad. Sci. 1999, Vol. 96, p. 9236-9241 proposes a technique called “digital PCR” for accurately quantifying trace amounts of nucleic acid chain. In digital PCR, a sample containing the detection target nucleic acid chain is subjected to limiting dilution with a reaction solution, and dispensed in a plurality of reaction sites (wells) for PCR reaction. The number of wells that show fluorescence out of the amplification product is then counted using, for example, fluorescent probes. Because it can be assumed by limiting dilution that each well contains at most only one molecule (one copy) of the detection target nucleic acid chain, the copy number of the detection target nucleic acid chain contained in a sample can be quantified based on the number of wells showing fluorescence.

JP-A-2001-269196 proposes a digital PCR-based nucleic acid quantification method that makes use of a plate including several thousand to several million channels (reaction sites), each containing one copy of the detection target nucleic acid chain contained in a sample. With this method, it is considered possible to accurately quantify the copy number of the detection target nucleic acid chain, because the method does not involve a mismatch between the number of fluorescing wells and the copy number of the detection target nucleic acid chain, which occurs when one channel contains more than one copy of the detection target nucleic acid chain.

SUMMARY

As described above, the digital PCR enables accurate quantification of the copy number of the detection target nucleic acid chain in a sample. Concerning the nucleic acid amplification methods intended to quantify the amount of nucleic acid chain, there are demands, particularly in the diagnoses of infections, for the measurement of the approximate amount of pathogen genome in a sample to examine the pathogen levels and determine the severity or developmental stage of the infection or disease. Such semi-quantitative measurement is also desired in gene expression level analyses intended not to accurately measure mRNA copy numbers but to simply examine mRNA expression levels.

Accordingly, there is a need for a technique that enables an easy measurement of the approximate amount of the detection target nucleic acid chain contained in a sample.

An embodiment is directed to a nucleic acid quantification method that uses a microchip for nucleic acid amplification reaction, the microchip including an inlet through which a liquid is introduced from outside, a plurality of reaction regions provided as reaction sites of a nucleic acid amplification reaction, and a channel through which the liquid introduced through the inlet is supplied into each of the reaction regions, wherein the likelihood of the nucleic acid amplification reaction varies between the reaction regions, the method including: flowing a detection target nucleic acid chain-containing solution through the channel and introducing the solution into each of the reaction regions to perform a nucleic acid amplification reaction; and detecting an amplification product in each of the reaction regions to specify the reaction regions in which the nucleic acid amplification reaction occurred.

The nucleic acid quantification method can measure the approximate amount of the detection target nucleic acid chain in the solution based on the likelihood of the nucleic acid amplification reaction in the specified reaction region. Specifically, the nucleic acid quantification method can determine that the solution contains larger amounts of detection target nucleic acid chain, when the specified reaction region is one in which the nucleic acid amplification reaction is less likely to occur.

In the nucleic acid quantification method, the reaction regions of the microchip for nucleic acid amplification reaction may have different inner volumes or may store beforehand at least some of the necessary reaction substances in different amounts so as to vary the likelihood of the nucleic acid amplification reaction between the reaction regions. The necessary reaction substances stored beforehand in the reaction regions may be oligonucleotide primers and/or an enzyme.

Another embodiment is directed to a microchip for nucleic acid amplification reaction, the microchip including: an inlet through which a liquid is introduced from outside; a plurality of reaction regions provided as reaction sites of a nucleic acid amplification reaction; and a channel through which the liquid introduced through the inlet is supplied into each of the reaction regions, wherein the likelihood of the nucleic acid amplification reaction varies between the reaction regions.

The microchip for nucleic acid amplification reaction may be configured so that the reaction regions have different inner volumes or store beforehand at least some of the necessary reaction substances in different amounts so as to vary the likelihood of the nucleic acid amplification reaction between the reaction regions.

In the microchip for nucleic acid amplification reaction, the channel may connect the reaction regions so that the liquid introduced into one of the reaction regions is successively introduced into the adjacent reaction region by overflowing the channel.

As used herein, “nucleic acid amplification reaction” encompasses both PCR reactions that involve temperature cycles including the three steps of heat denaturation, annealing, and extension reaction, and various isothermal amplification reactions that do not involve temperature cycles. Examples of isothermal amplification reactions include LAMP (Loop-Mediated Isothermal Amplification), SMAP (SMartAmplification Process), NASBA (Nucleic Acid Sequence-Based Amplification), ICAN® (Isothermal and Chimeric primer-initiated Amplification of Nucleic acids), a TRC (transcription-reverse transcription concerted) method, SDA (strand displacement amplification), TMA (transcription-mediated amplification), and RCA (rolling circle amplification). The "nucleic acid amplification reaction" also includes a wide range of nucleic acid amplification reactions involving or not involving temperature changes and intended for nucleic acid amplification.

The technique provided by the embodiments enables an easy measurement of the approximate amount of the detection target nucleic acid chain contained in a sample.

Additional features and advantages are described herein, and will be apparent from the following Detailed Description and the figures.

DETAILED DESCRIPTION

Embodiments of the present application will be described below in detail with reference to the drawings.

It should be noted that the embodiments below are merely an illustrative representation, and should not be construed to narrow the scope. Descriptions will be given in the following order.

Figure 1:
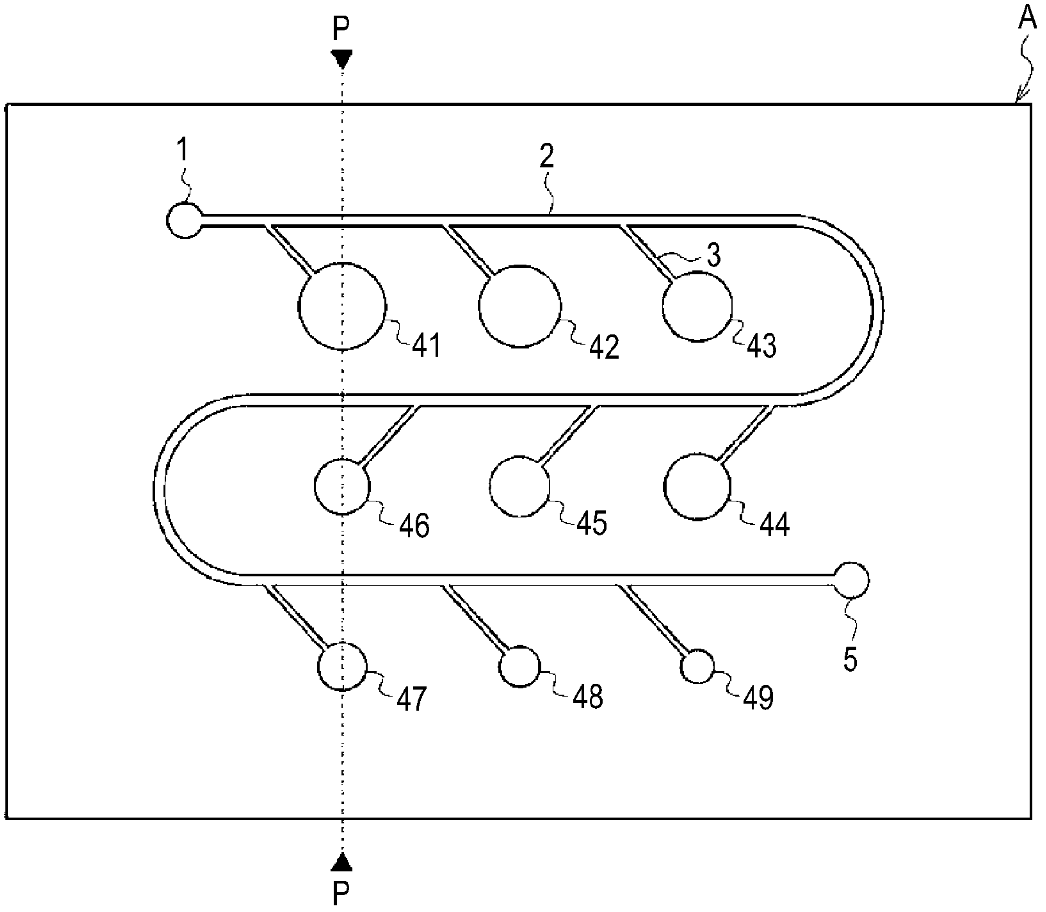
FIG. 1 is a top schematic view explaining the configuration of a microchip A for nucleic acid amplification reaction according to First Embodiment.
Figure 2:
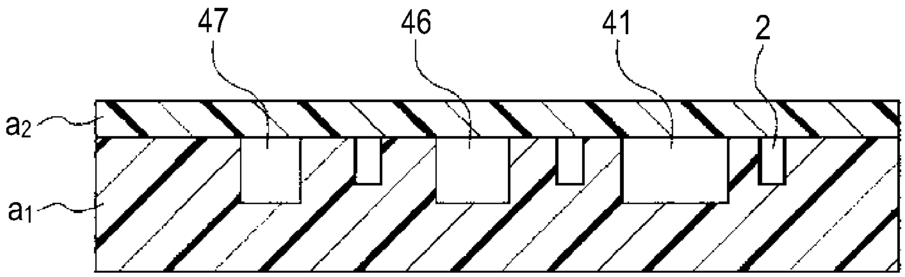
FIG. 2 is a cross sectional schematic view explaining the configuration of microchip A.

1. A nucleic acid quantification method and a microchip for nucleic acid amplification reaction according to First Embodiment (1) A microchip for nucleic acid amplification reaction (2) A nucleic acid quantification method 2. A nucleic acid quantification method and a microchip for nucleic acid amplification reaction according to Second Embodiment (1) A microchip for nucleic acid amplification reaction (2) A nucleic acid quantification method 3. A nucleic acid quantification method and a microchip for nucleic acid amplification reaction according to Third Embodiment (1) A microchip for nucleic acid amplification reaction (2) A nucleic acid quantification method 1. Nucleic Acid Quantification Method and Microchip for Nucleic Acid Amplification Reaction According to First Embodiment (1) Microchip for Nucleic Acid Amplification Reaction FIG. 1 and FIG. 2 are schematic views explaining the configuration of a microchip for nucleic acid amplification reaction (hereinafter, also referred to simply as "microchip") according to First Embodiment. FIG. 1 is a top schematic view; FIG. 2 is a cross sectional schematic view taken at P-P in FIG. 1.

A microchip A includes an inlet 1 through which a liquid (sample solution) is introduced from outside, a main channel 2 in communication with the inlet 1 at one end, branched channels 3 branching out of the main channel 2, and a plurality of wells 41 to 49 (reaction regions) as the reaction sites of nucleic acid amplification reaction. The other end of the main channel 2 is in communication with an outlet 5 through which the sample solution discharges to outside. The branched channels 3 branch out of the main channel 2 and are connected to the wells over the distance of the main channel 2 from the portion in communication with the inlet 1 to the portion in communication with the outlet 5. Note that, in the microchip A, the outlet 5 is not an essential element, and the microchip A may be configured not to discharge the sample solution introduced through the inlet 1.

The sample solution sent into the main channel 2 through the inlet 1 flows through the branched channels 3, and is successively introduced into the wells, from the well 41 proximal to the inlet 1 (upstream in the direction of liquid flow) to the well 49 proximal to the outlet 5 (downstream in the direction of liquid flow). The sample solution contains the detection target nucleic acid chain, which may be, for example, DNA, genomic RNA, or mRNA. The sample solution may also contain reagents necessary for the nucleic acid amplification reaction, including oligonucleotide primers (hereinafter, also referred to simply as "primers"), enzymes, nucleic acid monomer (dNTP), and reaction buffer (buffer) solutes.

The wells 41 to 49 become progressively smaller in inner volume from the well 41 on the upstream side toward the well 49 disposed downstream in the direction of liquid flow, so that the volume of the sample solution introduced into the wells becomes smaller toward the outlet 5 away from the inlet 1. The wells 41 to 49 are formed so that their inner volumes become progressively smaller along the direction of liquid flow by a factor of, for example, about 0.9 to 0.01, preferably about 0.5 to 0.1.

The likelihood of a nucleic acid amplification reaction in each well (reaction efficiency) is dependent on the amount of the detection target nucleic acid chain introduced into the well. The amount of the detection target nucleic acid chain introduced into each well is dependent on the volume of the sample solution introduced into the well, specifically on the inner volume of the well. Thus, the nucleic acid amplification reaction in each well becomes less likely to occur with the progressively decreasing inner volumes of the wells from the well 41 on the upstream side toward the well 49 disposed downstream in the direction of liquid flow.

The microchip A is configured as a laminate of a substrate layer a1 and a substrate layer a2. The inlet 1, the main channel 2, the branched channels 3, the wells 41 to 49, and the outlet 5 are formed in the substrate layer a1. The substrate layers a1 and a2 may be formed of material such as glass and various plastics (polypropylene, polycarbonate, cycloolefin polymer, polydimethylsiloxane). For optical detection of the amplification product in the wells, the substrate layers a1 and a2 should preferably be made of light transmissive material that shows a weak self-fluorescence, and has small wavelength dispersion and thus small optical errors. The inlet 1 and other elements may be formed in the substrate layer a2, or may be formed in part in both the substrate layer a1 and the substrate layer a2. Further, more than one substrate layers may be used to form the microchip.

(2) Nucleic Acid Quantification Method

A nucleic acid quantification method according to First Embodiment using the microchip A is described below.

First, the sample solution is sent into the main channel 2 through the inlet 1, and introduced into the wells 41 to 49 to perform a nucleic acid amplification reaction, such as a PCR reaction and a LAMP reaction, according to an ordinary method. For example, in PCR, predetermined temperature cycles including the three steps of heat denaturation, annealing, and extension reaction are performed to run a nucleic acid amplification reaction. In LAMP, for example, a nucleic acid amplification reaction is run at the maintained predetermined reaction temperature.

As described above, the microchip A is configured to include the wells that become progressively smaller in inner volume from the well 41 on the upstream side toward the well 49 disposed downstream in the direction of liquid flow, so that the nucleic acid amplification reaction in each well becomes progressively less likely to occur in this order. Thus, according to this procedure, the nucleic acid amplification reaction proceeds further down to the downstream wells along the direction of liquid flow as the amount of the detection target nucleic acid chain contained in the sample solution increases. On the other hand, the reaction does not proceed further beyond the upstream wells along the direction of liquid flow when the amount of the detection target nucleic acid chain contained in the sample solution is small.

The amplification product in each well is then detected to specify the wells in which the nucleic acid amplification reaction has occurred. The amplification product may be detected with a fluorescent dye or a fluorescent dye-labeled fluorescent probe, by detecting the fluorescence of the fluorescent dye that fluoresces in response to the formation of the amplification product. The wells involving the nucleic acid amplification reaction may be specified by automatically measuring the fluorescence signal from the fluorescent dye in each well through analysis of the obtained fluorescent image of the microchip A using an image processing system. The wells involving the nucleic acid amplification reaction may also be specified by checking the presence or absence of a fluorescence from each well, either by visually inspecting the image or by observing the microchip A with, for example, a fluorescence microscope.

Finally, the amount of the detection target nucleic acid chain contained in the sample solution is measured based on the likelihood of the nucleic acid amplification reaction in the specified wells. In the microchip A, the nucleic acid amplification reaction proceeds further down to the downstream wells along the direction of liquid flow as the amount of the detection target nucleic acid chain contained in the sample solution increases. Thus, the amount of the detection target nucleic acid chain contained in the sample solution can be determined by specifying the wells in which the nucleic acid amplification reaction has occurred. Specifically, when the nucleic acid amplification reaction has occurred in the wells 41 and 42, the sample solution can be determined as containing a larger amount of detection target nucleic acid chain than when the reaction has occurred only in the well 41. By the same reasoning, the sample solution can be determined as containing a larger amount of detection target nucleic acid chain when the nucleic acid amplification reaction has occurred in the wells further down beyond the well 41 along the direction of liquid flow.

The amount of the detection target nucleic acid chain contained in the sample solution can be measured even more accurately when a relationship between detection target nucleic acid chain amount and the wells (or the well volumes) that involve nucleic acid amplification reaction is acquired beforehand using solutions that contain known amounts of detection target nucleic acid chain.

As described above, the nucleic acid quantification method according to the present embodiment can measure the approximate amount of the detection target nucleic acid chain contained in the sample solution by specifying the wells that involve the nucleic acid amplification reaction performed with the microchip in which the likelihood of a nucleic acid amplification reaction varies.

The present embodiment has been described through the case of arranging a total of 9 wells (3 rows×3 columns) at regular intervals in the microchip. However, any number of wells can be disposed in any layout, and the well shape is not limited to the columnar shape shown in the figures. Further, the channel configuration by which the sample solution introduced through the inlet 1 is supplied to each well is not limited to the configuration of the main channel 2 and the branched channels 3 shown in the figures.

Further, even though the present embodiment has been described through the case of decreasing (or increasing) the inner volume by varying the well area, the inner volume of the well may be decreased by varying the depth. Further, the sequence of the wells of different inner volumes is not limited to the progressively smaller volumes from the upstream to the downstream side along the direction of liquid flow.

Figure 3:
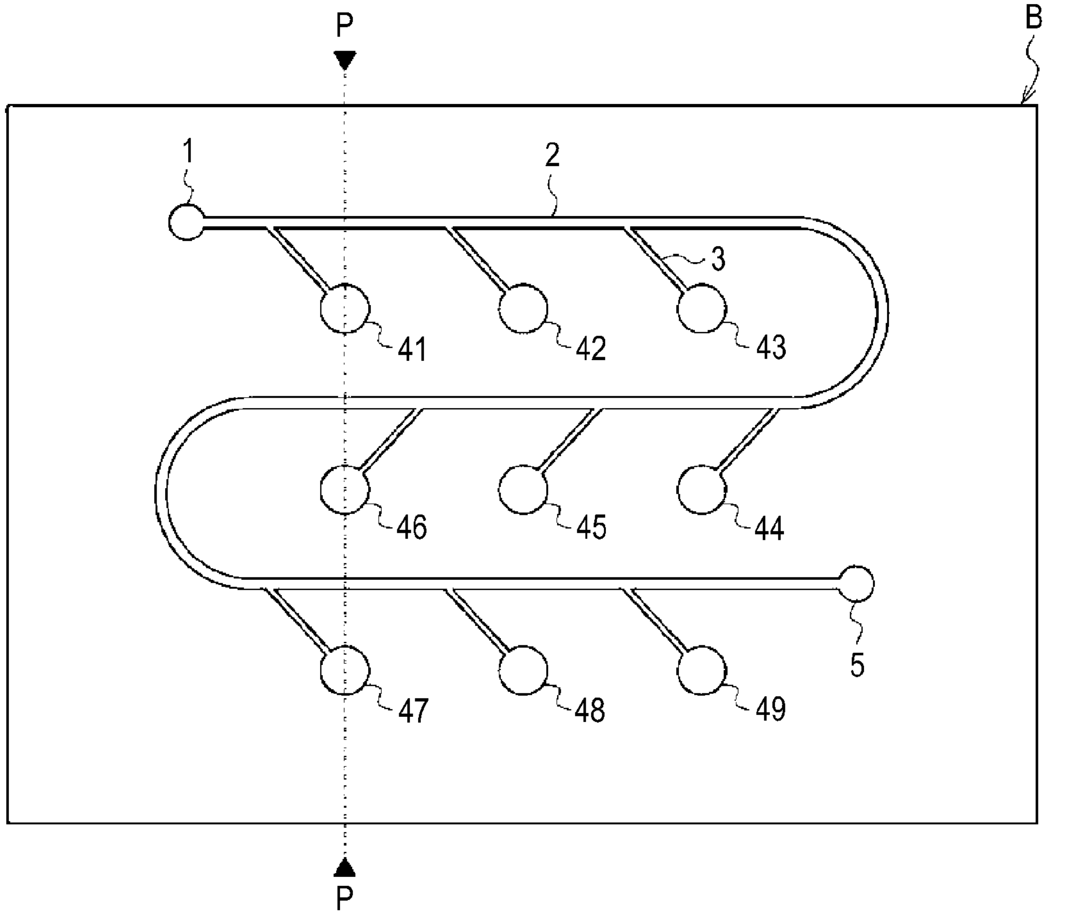
FIG. 3 is a top schematic view explaining the configuration of a microchip B for nucleic acid amplification reaction according to Second Embodiment.

2. Nucleic Acid Quantification Method and Microchip for Nucleic Acid Amplification Reaction According to Second Embodiment (1) Microchip for Nucleic Acid Amplification Reaction FIG. 3 is a top schematic view explaining the configuration of a microchip for nucleic acid amplification reaction (hereinafter, also referred to simply as "microchip") according to Second Embodiment.

A microchip B includes an inlet 1 through which a sample solution is introduced from outside, a main channel 2 in communication with the inlet 1 at one end, branched channels 3 branching out of the main channel 2, and a plurality of wells 41 to 49 as the reaction sites of nucleic acid amplification reaction. The other end of the main channel 2 is in communication with an outlet 5 through which the sample solution discharges to outside. The branched channels 3 branch out of the main channel 2 and are connected to the wells over the distance of the main channel 2 from the portion in communication with the inlet 1 to the portion in communication with the outlet 5. Note that, in the microchip B, the outlet 5 is not an essential element, and the microchip B may be configured not to discharge the sample solution introduced through the inlet 1.

The sample solution sent into the main channel 2 through the inlet 1 flows through the branched channels 3, and is successively introduced into the wells, from the well 41 proximal to the inlet 1 (upstream in the direction of liquid flow) to the well 49 proximal to the outlet 5 (downstream in the downstream in the direction of liquid flow). The sample solution contains the detection target nucleic acid chain, which may be, for example, DNA, genomic RNA, or mRNA.

In the wells 41 to 49, at least some of the substances required for the nucleic acid amplification reaction are stored in advance in different amounts. The substances stored beforehand in the wells are those required to obtain an amplification product in the nucleic acid amplification reaction, specifically, for example, primers, enzymes, nucleic acid monomer, and reaction buffer solutes. One or more of these substances may be stored in the wells, and the remaining substances are introduced into the wells through the inlet 1 with the sample solution.

Figure 4C:
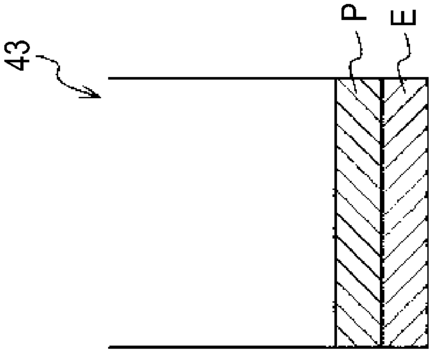
FIGS. 4A to 4C are schematic views explaining the necessary nucleic acid amplification reaction substances present in the wells of microchip B.
Figure 4B:
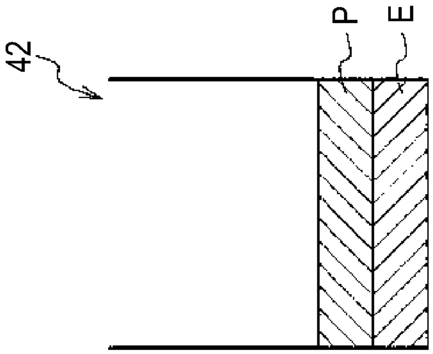
Figure 4A:
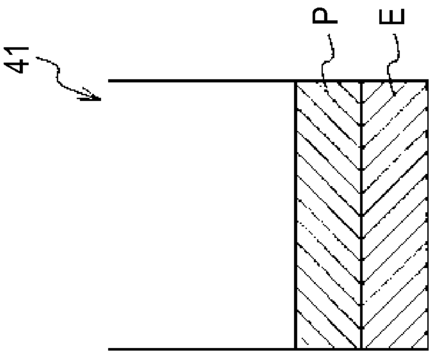

FIGS. 4A to 4C represent an example in which primers and enzyme are stored in the wells in different amounts. In the wells 41 to 49, the amounts of primer P and enzyme E become progressively smaller from the well 41 on the upstream side toward the well 49 disposed downstream in the direction of liquid flow. In the figures, the amounts of primer P and enzyme E are varied by progressively reducing the thicknesses of the primer P and enzyme E layers in the wells 41, 42, and 43.

The primer P and enzyme E are stored in the wells 41 to 49 in such a manner that the primer and enzyme amounts become progressively smaller along the direction of liquid flow by a factor of, for example, about 0.9 to 0.01, preferably about 0.5 to 0.1.

The likelihood of a nucleic acid amplification reaction (reaction efficiency) in each well is dependent on the amounts of the necessary reaction substances stored in the wells. Thus, the nucleic acid amplification reaction in each well becomes less likely to occur with the progressively decreasing amounts of primer P and enzyme E from the well 41 on the upstream side toward the well 49 disposed downstream in the direction of liquid flow.

(2) Nucleic Acid Quantification Method

A nucleic acid quantification method according to Second Embodiment using the microchip B is described below.

First, the sample solution is sent into the main channel 2 through the inlet 1, and introduced into the wells 41 to 49. As a result, the necessary reaction substances (here, primer P and enzyme E) stored in advance in the wells mix with the remaining substances and the detection target nucleic acid chain contained in the sample solution. After the introduction of the sample solution, a nucleic acid amplification reaction such as a PCR reaction and a LAMP reaction is performed according to an ordinary method. For example, in PCR, predetermined temperature cycles including the three steps of heat denaturation, annealing, and extension reaction are performed to run a nucleic acid amplification reaction. In LAMP, for example, a nucleic acid amplification reaction is run at the maintained predetermined reaction temperature.

As described above, the microchip B is configured to include the wells that contain progressively smaller amounts of the necessary reaction substances from the well 41 on the upstream side toward the well 49 disposed downstream in the direction of liquid flow, so that the nucleic acid amplification reaction in each well becomes progressively less likely to occur in this order. Thus, according to this procedure, the nucleic acid amplification reaction proceeds further down to the downstream wells along the direction of liquid flow as the amount of the detection target nucleic acid chain contained in the sample solution increases. On the other hand, the reaction does not proceed further beyond the upstream wells along the direction of liquid flow when the amount of the detection target nucleic acid chain contained in the sample solution is small.

The amplification product in each well is then detected to specify the wells in which the nucleic acid amplification reaction has occurred. The amplification product may be detected with a fluorescent dye or a fluorescent dye-labeled fluorescent probe, by detecting the fluorescence of the fluorescent dye that fluoresces in response to the formation of the amplification product. The wells involving the nucleic acid amplification reaction may be specified by automatically measuring the fluorescence signal from the fluorescent dye in each well through analysis of the obtained fluorescent image of the microchip B using an image processing system. The wells involving the nucleic acid amplification reaction may also be specified by checking the presence or absence of a fluorescence from each well, either by visually inspecting the image or by observing the microchip B with, for example, a fluorescence microscope.

Finally, the amount of the detection target nucleic acid chain contained in the sample solution is measured based on the likelihood of the nucleic acid amplification reaction in the specified wells. In the microchip B, the nucleic acid amplification reaction proceeds further down to the downstream wells along the direction of liquid flow as the amount of the detection target nucleic acid chain contained in the sample solution increases. Thus, the amount of the detection target nucleic acid chain contained in the sample solution can be determined by specifying the wells in which the nucleic acid amplification reaction has occurred. Specifically, when the nucleic acid amplification reaction has occurred in the wells 41 and 42, the sample solution can be determined as containing a larger amount of detection target nucleic acid chain than when the reaction has occurred only in the well 41. By the same reasoning, the sample solution can be determined as containing a larger amount of detection target nucleic acid chain when the nucleic acid amplification reaction has occurred in the wells further down beyond the well 41 along the direction of liquid flow.

The amount of the detection target nucleic acid chain contained in the sample solution can be measured even more accurately when a relationship between detection target nucleic acid chain amount and the wells (or the well volumes) that involve nucleic acid amplification reaction is acquired beforehand using solutions that contain known amounts of detection target nucleic acid chain.

As described above, the nucleic acid quantification method according to the present embodiment can measure the approximate amount of the detection target nucleic acid chain contained in the sample solution by specifying the wells that involve the nucleic acid amplification reaction performed with the microchip in which the likelihood of a nucleic acid amplification reaction varies.

In the present embodiment, any number of wells may be arranged in any layout, and the well shape is not limited to the columnar shape shown in the figure, as in the foregoing First Embodiment. Further, the sequence of the wells containing different amounts of necessary reaction substances is not limited to the progressively decreasing amounts from the upstream to the downstream wells in the direction of liquid flow.

Figure 5:
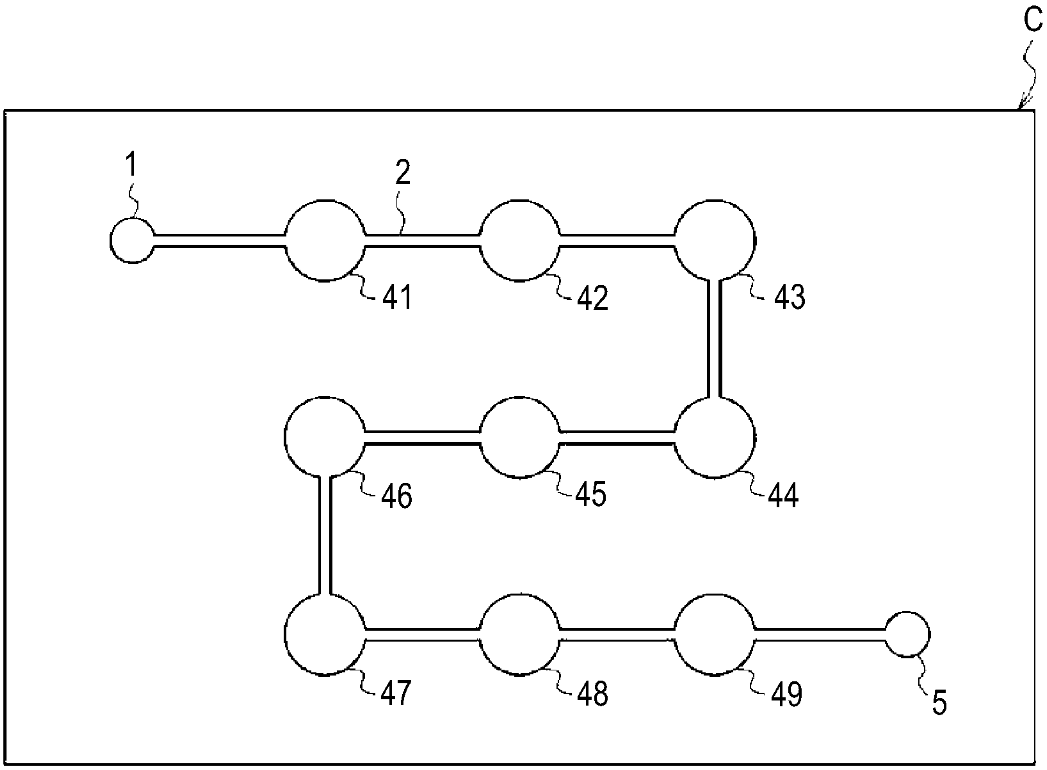
FIG. 5 is a top schematic view explaining the configuration of a microchip C for nucleic acid amplification reaction according to Third Embodiment.

Further, the channel configuration by which the sample solution introduced through the inlet 1 is supplied to each well is not limited to the configuration of the main channel 2 and the branched channels 3 shown in the figure. For example, a configuration without the branched channels may be used, as illustrated in FIG. 5. In a microchip C illustrated in FIG. 5, the wells 41 to 49 are arranged in communication with one another via the main channel 2 so that the sample solution introduced into one of the wells through the main channel 2 is successively introduced into the adjacent well by overflowing the main channel 2. The sample solution sent into the main channel 2 through the inlet 1 is first stored in the well 41 proximal to the inlet 1, and overflows from the well 41 into the adjacent well 42. In the same manner, the sample solution overflows the well 42, and is successively introduced into the downstream wells in the direction of liquid flow.

As with the microchip A, the microchip B may be configured as a laminate of two substrate layers. The substances required for the nucleic acid amplification reaction may be stored in the wells by dropping and drying reagents such as a primer solution and an enzyme solution in the wells after molding the inlet 1, the main channel 2, the branched channels 3, the wells 41 to 49, and the outlet 5 and before bonding the substrate layers.

The molding of the inlet 1 and the other elements may be performed by the wet etching or dry etching of a glass substrate layer, or by the nanoimprinting, injection molding, or cutting of a plastic substrate layer.

Preferably, reagents such as a primer solution and an enzyme solution are dried gradually by, for example, air drying, vacuum drying, or freeze drying. When the substance stored in the well is an enzyme, it is preferable that the dropped enzyme solution be dried by critical point drying, in order to prevent the enzyme activity from being lowered or deactivated. Fluorescent dyes or fluorescent dye-labeled fluorescent probes also may be stored in the wells for the detection of the amplification product. Here, the order in which reagents such as a primer solution and an enzyme solution are dropped and dried is not particularly limited, and the primers and enzyme are not necessarily required to be stored in layers as in FIGS. 4A to 4C.

The substrate layers may be bonded by methods that activate the substrate layer surfaces by, for example, an oxygen plasma treatment or a vacuum ultraviolet treatment. The oxygen plasma treatment and vacuum ultraviolet treatment are performed under appropriately set conditions according to the material of the substrate layers.

3. Nucleic Acid Quantification Method and Microchip for Nucleic Acid Amplification Reaction According to Third Embodiment (1) Microchip for Nucleic Acid Amplification Reaction A microchip for nucleic acid amplification reaction (hereinafter, also referred to simply as "microchip") according to Third Embodiment is described below. The configuration of the microchip for nucleic acid amplification reaction according to the present embodiment is essentially the same as that of the microchip B according to Second Embodiment, except for the substances stored in the microchip. Accordingly, descriptions will be given with reference to FIG. 3.

Referring to the figure, the microchip according to the present embodiment is essentially the same as the microchip according to Second Embodiment, except that at least one of the wells 41 to 49 is used as a correction well. The following descriptions thus mainly deal with the correction well. Specifically, for example, the well 49 will be described as the correction well. As used herein, the correction well is a well in which a nucleic acid chain of a known concentration is stored beforehand.

The correction well stores a nucleic acid chain of a known concentration for correction, in addition to enzyme E and primer P as in the other wells 41 to 48. Note that the correction nucleic acid chain may have completely or partially the same sequence as the detection target nucleic acid chain contained in the sample solution. When the detection target nucleic acid chain and the correction nucleic acid chain have the same sequences, for example, RNA and DNA are used for the detection target nucleic acid chain and the correction nucleic acid chain, respectively. Here, the wells 41 to 48 store reverse transcriptase and DNA polymerase, and the correction well stored DNA polymerase. On the other hand, when the correction nucleic acid chain and the correction nucleic acid chain have partially the same sequences, different primers corresponding to these sequences are stored in the correction well and the wells 41 to 48.

(2) Nucleic Acid Quantification Method

A nucleic acid quantification method according to Third Embodiment is described below. The nucleic acid quantification method according to Third Embodiment is essentially the same as the nucleic acid quantification method according to Second Embodiment, except that the well 49 in the wells 41 to 49 is used as the correction well. Accordingly, the following descriptions mainly deal with the use of the correction well.

Specifically, the nucleic acid amplification reaction proceeds as the sample solution sent through the inlet 1 is successively introduced into the wells, from the well 41 on the upstream side to the well 49 disposed downstream in the direction of liquid flow. In the correction well, the nucleic acid amplification reaction proceeds with the correction nucleic acid chain of a known concentration. The amplification product is then detected with a fluorescent dye or a fluorescent dye-labeled fluorescent probe, by detecting the fluorescence of the fluorescent dye that fluoresces in response to the formation of the amplification product.

There is a possibility that the sample solution introduced into the wells 41 to 49 contain components such as foreign substances and reaction inhibitors. Such foreign substances and reaction inhibitors influence reaction efficiency and cause measurement variations. However, in the microchip according to the present embodiment, the provision of the correction well storing the correction nucleic acid chain of a known concentration enables correction of such variations, and the concentration of the amplification product can be found from, for example, fluorescence intensity.

As described above, the nucleic acid quantification method according to the present embodiment uses one or more of the microchip wells as correction wells, and thus enables the influence of components such as foreign substances and reaction inhibitors in the detection target nucleic acid chain-containing sample solution to be grasped. More specifically, components such as foreign substances and reaction inhibitors originating in the sample have influences on reaction efficiency and varies the fluorescence intensity even in samples containing the same amount of detection target nucleic acid chain. Such variations can be corrected with the nucleic acid quantification method according to the present embodiment.

The correction well was described as being one of the wells, the well 49. However, more than one well may be used as correction wells. For example, a plurality of wells of different concentrations may be used as correction wells, and when the detection target nucleic acid chain and the correction nucleic acid chain have the same sequences, the amount of the detection target nucleic acid chain contained in the sample solution may be measured from a standard curve created based on the measured fluorescence intensities of the correction wells.

The correction well, described as being one of the wells of the microchip B in the present embodiment, may be one or more wells of the microchip A according to First Embodiment.

EXAMPLES

Nucleic acid was quantified according to the following procedure, using a common RT-PCR method and the method according to the embodiment.

A wiped nasal fluid (17 specimens) obtained from patients with possible influenza infection was suspended in a buffer (130 μL). A half amount of the suspension was then mixed with a commercially available influenza virus extraction reagent (Eiken Chemical Co., Ltd.; Cat. No. LMP801). Then, a RAMP reaction was performed for the influenza genome in the mixture, using a commercially available primer set (Eiken Chemical Co., Ltd.; Cat. No. PM0021) and a RT-RAMP kit (Eiken Chemical Co., Ltd.; Cat. No. LMP244). The reaction was performed with a real time RT-PCR apparatus (Chromo 4; Bio-Rad) and the microchip (9 wells). The wells that showed increased fluorescence intensity within 30 min from the start of the RAMP reaction were determined as influenza genome positive.

Separately, the influenza genome was purified from a half amount of the wiped nasal fluid suspension, using a commercially available RNA extraction kit (QIAGEN; Cat. No. 52904), and a RT-PCR analysis was performed according to the protocol recommended by WHO (WHO information for laboratory diagnosis of pandemic (H1N1) 2009 virus in human—revised, 23 Nov. 2009).

Figure 6:
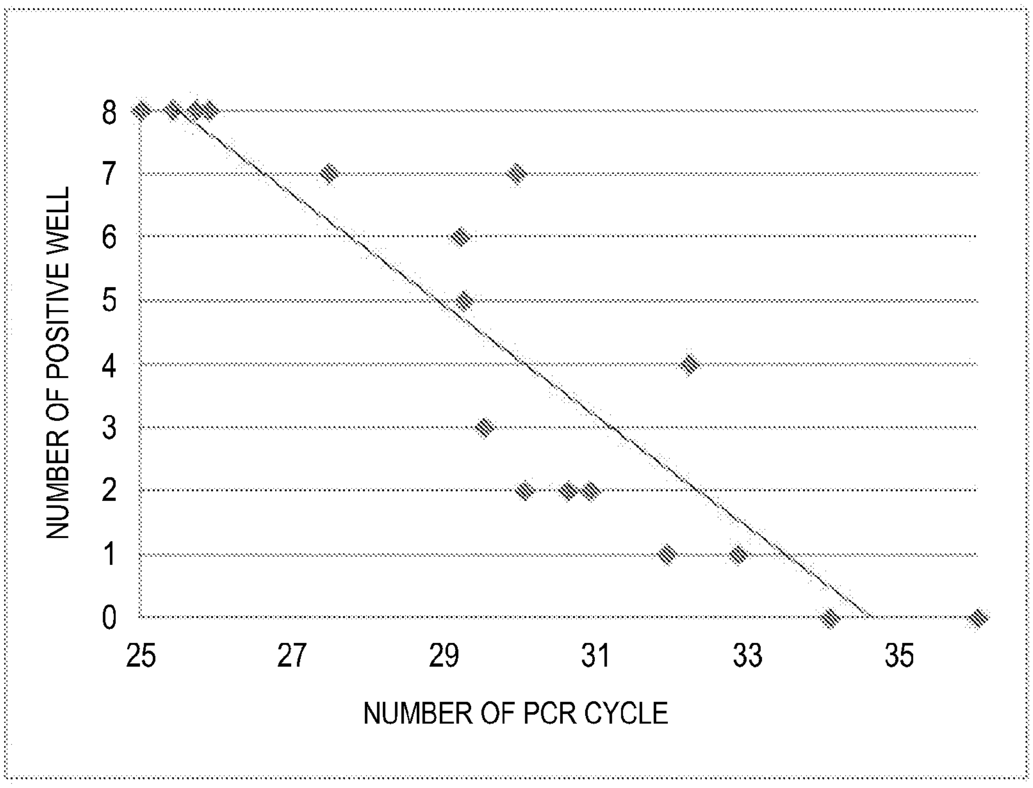
FIG. 6 is a graph representing the result of influenza virus genome quantification.

The results are presented in FIG. 6. The vertical axis represents the number of positive wells that showed increased fluorescence intensity within 30 min from the start of the RAMP reaction. The horizontal axis represents the number of detection cycles in RT-PCR analysis. The results demonstrated a correlation between the number of RT-PCR detection cycles and the number of positive wells, and suggest that the influenza genome in the specimens can be quantified from the number of positive wells.

The nucleic acid quantification method according to the embodiment can conveniently measure the approximate amount of the detection target nucleic acid chain contained in a sample. The nucleic acid quantification method according to the embodiment can thus be used for the measurement of the approximate amount of pathogen genome in a sample to determine pathogen levels, and is therefore particularly useful for easy diagnosis of the severity and the developmental stage of infections.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A nucleic acid quantification method that uses a microchip for nucleic acid amplification reaction, the microchip including an inlet through which a liquid is introduced from outside, a plurality of reaction regions provided as reaction sites of a nucleic acid amplification reaction, and a channel through which the liquid introduced through the inlet is supplied into each of the reaction regions, the method comprising:

flowing a solution containing a target nucleic acid through the channel and introducing the solution into each of the reaction regions to perform a nucleic acid amplification reaction; and detecting an amplification product in each of the reaction regions to specify the reaction regions in which the nucleic acid amplification reaction occurred, wherein the reaction regions of the microchip have progressively smaller inner volumes from an upstream side to a downstream side of the channel so as to vary the likelihood of the nucleic acid amplification reaction between the reaction regions.

* * * * *